United States Patent [19]
Takashima et al.

[11] Patent Number: 6,084,144
[45] Date of Patent: Jul. 4, 2000

[54] METHOD OF RECOVERING BORON TRIFLUORIDE COMPLEX AND PROCESS FOR PRODUCING OLEFIN OLIGOMER USING THE SAME

[75] Inventors: Tsutomu Takashima, Kawasaki; Yoshisuke Kakuyama; Shigeru Nishikida, both of Yokohama; Yuichi Tokumoto, Kawasaki; Kouji Fujimura, Kisarazu, all of Japan

[73] Assignee: Nippon Petrochemicals Company, Limited, Tokyo, Japan

[21] Appl. No.: 09/171,343
[22] PCT Filed: Feb. 26, 1998
[86] PCT No.: PCT/JP98/00783
 § 371 Date: Oct. 15, 1998
 § 102(e) Date: Oct. 15, 1998
[87] PCT Pub. No.: WO98/38225
 PCT Pub. Date: Mar. 9, 1998

[30] Foreign Application Priority Data

Feb. 26, 1997 [JP] Japan ................... 9-057094
Feb. 26, 1997 [JP] Japan ................... 9-057095

[51] Int. Cl.⁷ .................. C07C 2/08; C07C 2/22
[52] U.S. Cl. ............ 585/525; 585/521; 585/465
[58] Field of Search ................ 585/525, 521, 585/465

[56] References Cited

U.S. PATENT DOCUMENTS

| | | |
|---|---|---|
| 2,167,358 | 7/1939 | Gleason . |
| 2,997,371 | 8/1961 | Wadsworth et al. . |
| 3,382,291 | 5/1968 | Brennan ................ 585/521 |
| 4,152,499 | 5/1979 | Boerzel et al. ............ 526/52.4 |
| 4,227,027 | 10/1980 | Booth et al. ............ 585/465 |
| 4,263,467 | 4/1981 | Madgavkar et al. . |
| 4,384,162 | 5/1983 | Vogel et al. . |
| 4,454,366 | 6/1984 | Vogel et al. ............ 585/525 |
| 4,479,023 | 10/1984 | Marty et al. ............ 585/321 |
| 4,956,512 | 9/1990 | Nissfolk et al. ............ 585/521 |
| 4,956,513 | 9/1990 | Walker et al. . |
| 4,981,578 | 1/1991 | Tycer et al. ............ 208/262.1 |
| 5,254,784 | 10/1993 | Nurminen et al. . |
| 5,811,616 | 9/1998 | Holub et al. ............ 585/404 |
| 5,846,429 | 12/1998 | Shimizu et al. . |

FOREIGN PATENT DOCUMENTS

| | | |
|---|---|---|
| 0 145 235 B1 | 1/1988 | European Pat. Off. . |
| 0 791 557 A1 | 8/1997 | European Pat. Off. . |
| 2-45429 | 2/1990 | Japan . |
| 2-149533 | 6/1990 | Japan . |
| 4-331720 | 11/1992 | Japan . |
| 5-115786 | 5/1993 | Japan . |
| 06287211 | 10/1994 | Japan . |
| WO 85/01942 | 5/1985 | WIPO . |

Primary Examiner—Walter D. Griffin
Assistant Examiner—Tam M. Nguyen
Attorney, Agent, or Firm—Hollander Law Firm, P.L.C.

[57] ABSTRACT

A boron trifluoride complex can be recovered without changing its molar coordination ratio, by applying a direct and/or alternating voltage to an electrically-nonconductive fluid in which at least a part of boron trifluoride complex is dispersed and/or dissolved, and separating the boron trifluoride complex by settling from the electrically-nonconductive fluid. By utilizing this method for the preparation of olefin oligomer using a boron trifluoride complex catalyst, it is possible to reuse the recovered catalyst as it stands for the reaction.

10 Claims, 1 Drawing Sheet

Boron Trifluoride/Diethyl Ether Complex
13C-NMR Spectra of (1:1 mole adduct)

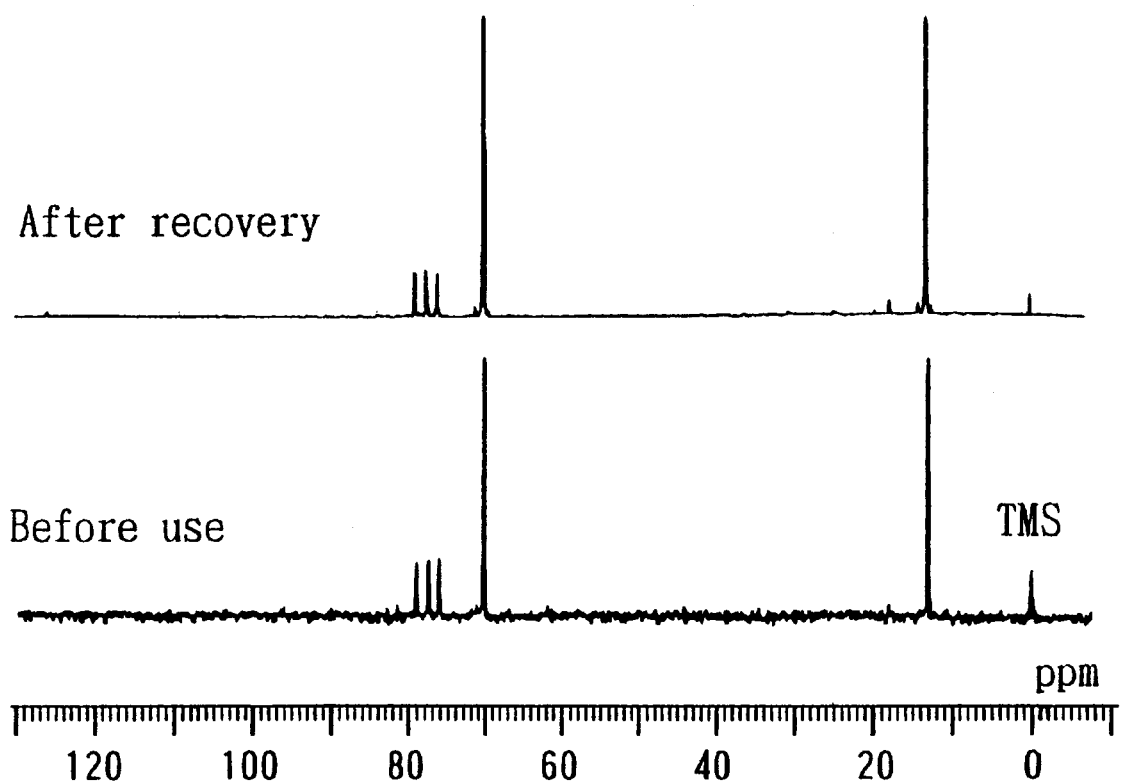

METHOD OF RECOVERING BORON TRIFLUORIDE COMPLEX AND PROCESS FOR PRODUCING OLEFIN OLIGOMER USING THE SAME

TECHNICAL FIELD

This invention relates to a method of recovering a boron trifluoride complex such as a catalyst which is dispersed and/or dissolved in a fluid, and a process for producing olefin oligomers using the same.

BACKGROUND ART

Boron trifluoride complex catalysts composed of boron trifluoride and a complexing agent, ligand, are used widely in industrial fields as catalysts for various chemical reactions such as alkylation, isomerization, polymerization, decomposition and dehydration. These complex catalysts are utilized in the form of various complexing agents coordinated to boron trifluoride in appropriate ratios for objective reactions.

After the reaction using a boron trifluoride complex catalyst, it is necessary to separate the complex catalyst from the reaction mixture. For this purpose, a method is usually made used of neutralizing the catalyst with an aqueous solution of basic substance such as ammonia or caustic soda, and then washing with water.

Disclosed in U.S. Pat. No. 4,227,027 is another method which comprises adding a polyhydric alcohol having two or more hydroxyl groups to the reaction mixture containing a boron -trifluoride complex catalyst, causing addition reaction of the alcohol with only boron trifluoride in the complex catalyst to remove boron trifluoride, and decomposing the addition product by heating to recover boron trifluoride.

Furthermore, Japanese Laid-Open Patent Publication No. 6-287211 discloses a method of reaction using a boron trifluoride complex catalyst, which comprises heating a reaction mixture to vaporize boron trifluoride gas, contacting the boron trifluoride gas with a complexing agent in excess relative to boron trifluoride to form a new complex, and recycling it into the reactor for reuse.

In these methods, however, the boron trifluoride is separated and recovered solely, so that an additional complexing step is necessary for the reuse of complex catalyst, with the result that a multi-stage process is necessary and the increase of costs is caused. As for the method disclosed in Japanese Laid-Open Patent Publication No. 6-287211, the reaction mixture is heated in coexistence with a boron trifluoride complex catalyst, which has bad influence on the composition of reaction mixture and restrict its use severely.

Japanese Laid-Open Patent Publication No. 2-45429 discloses a method of carrying out alkylation reaction between olefins and aromatic compounds using a boron trifluoride ether complex, which comprises adding 0.05–2 mol of weak acids such as phosphoric acid, acetic acid and phenol to a boron trifluoride ether complex in the reaction system at room temperature at any stage before or after the reaction, then separating the catalyst by settling in the reaction mixture, and using the separated catalyst as it stands in the next alkylation reaction.

In this case, however, the recovered complex is not an initial boron trifluoride ether complex catalyst, but a boron trifluoride/weak acid complex catalyst in which ether as complexing agent has been replaced with a weak acid added later. Further, the recovery is as low as about 27% by weight.

Olefins having vinylidene structures as double bonds in oligomer are utilized effectively, because they react with maleic acid or else at a high rate. Therefore, several methods have been proposed which introduce much more vinylidene structures into oligomer.

For example, U.S. Pat. No. 4,152,499 discloses a polymerization method in which isobutene is polymerized in the range of temperature from −50° C. to +30° C. to produce polyisobutene having polymerization degree of 10–100 by using a gaseous boron trifluoride catalyst or a boron trifluoride complex catalyst made by complexing with water or alcohol. This method shows that it is possible to introduce 60–90% of vinylidene double bonds at terminal positions.

European Patent 0 145 235 A discloses that polyisobutene is obtained by using a boron trifluoride alcohol complex catalyst comprised of boron trifluoride and $C_1$–$C_8$ alcohols, and describes that it is possible to introduce 70–90% of vinylidene double bonds at terminal positions.

In the production of olefin oligomers as the above, a boron trifluoride complex catalyst is generally used, which has each particular complexing agent selected and its molar coordination number is specified. Thus, ligands bound in a complex demonstrate the desired catalyst functions by specifying the coordination number. Therefore, when a complex catalyst is recovered and reused, it is necessary to recover the complex without any change in coordination number. If the coordination number is varied in recovering, the catalyst function changes, and its readjustment must be carried out after recovering. Therefore, the above recovering method is not preferable.

However, as the coordination number is susceptible to conditions such as temperature and others, the recovering and the reusing of complex catalysts have scarcely been done in the production of olefin oligomer using a boron trifluoride complex catalyst.

The object of the present invention is to provide a method for recovering a boron trifluoride complex as it stands, for example, in the state of maintaining activity of a catalyst, from an electrically-nonconductive fluid containing the complex dispersed and/or dissolved therein, and a process for producing olefin oligomer characterized by recovering and reusing the complex catalyst.

DISCLOSURE OF INVENTION

A first feature of the present invention relates to a method of recovering a boron trifluoride complex which comprises applying a direct and/or alternating voltage to an electrically-nonconductive fluid in which boron trifluoride complex is dispersed and/or dissolved, thereby separating the boron trifluoride complex by settling it from the electrically-nonconductive fluid, and then recovering the separated complex.

A second feature of the present invention relates to a method of recovering a boron trifluoride complex in the above first feature, wherein electric field strength of direct and/or alternating voltage is in the range of 0.001–40 kV/mm.

A third feature of the present invention relates to a method of recovering a boron trifluoride complex in the above first feature, wherein the temperature of the electrically-nonconductive fluid while applying a direct and/or alternating voltage is in the range from −100° C. to +50° C.

A fourth feature of the present invention relates to a method of recovering a boron trifluoride complex in the above first feature, wherein the complexing agent which forms a complex with boron trifluoride is a polar compound.

A fifth feature of the present invention relates to a method of recovering a boron trifluoride complex in the above fourth feature, wherein the polar compound is the one selected from the group consisting of water, alcohols, ethers, phenols, ketones, aldehydes, esters, acid anhydrides and acids.

A sixth feature of the present invention relates to a method of recovering a boron trifluoride complex in the above first feature, wherein the molar ratio of boron trifluoride to complexing agent in the complex is in the range from 0.01:1 to 2:1.

A seventh feature of the present invention relates to a method of recovering a boron trifluoride complex in the above first feature, wherein the electrically-nonconductive fluid is a hydrocarbon fluid.

An eighth feature of the present invention relates to a process for producing olefin oligomer which comprises the following steps from (I) to (IV), (I) polymerizing olefin in a liquid phase in the presence of a boron trifluoride complex catalyst comprised of boron trifluoride and a complexing agent, (II) after polymerization, applying a direct and/or alternating voltage to a reaction mixture in which boron trifluoride complex catalyst is at least partially dispersed and/or dissolved, thereby separating the complex catalyst by settling owing to the difference of specific gravity, (III) recovering the separated complex catalyst by settling from the reaction mixture, and (IV) polymerizing olefin in liquid phase by using at least a part of the recovered complex catalyst.

A ninth feature of the present invention relates to a process for producing olefin oligomer in the above eighth feature, wherein the concentration of olefin in a feed mixture in the liquid phase polymerization is 5% by weight or more.

A tenth feature of the present invention relates to a process for producing olefin oligomer in the above eighth feature, wherein the molecular weight of the olefin oligomer is in the range of 100–100,000.

According to the present invention, it is possible to recover a complex catalyst easily without changing the molar ratio of boron trifluoride complex only by applying an electric field. As a result, the recovered complex can be reused.

Further, the above method can be applied in the production of olefin oligomer using a boron trifluoride complex catalyst. That is, it is possible to apply an electric voltage to the reaction mixture after polymerization, to separate the boron trifluoride complex catalyst by settling from the reaction mixture, to recover the complex catalyst without any change in coordination number of ligands, and to reuse it as it stands.

The amount of boron trifluoride used in cation polymerization of olefin is usually 0.0001–0.5 mol per 1 mol of olefin components to be polymerized. After the reactions as the above, at least a part of boron trifluoride complex catalyst is stably dissolved or dispersed in the reaction mixture, and it is very difficult to recover the dissolved or dispersed complex catalyst like this. Therefore, it is very hard to separate boron trifluoride complex catalyst as it stands from the reaction mixture and to reuse it. The present invention relates to a skill for recovering a complex catalyst dissolved or dispersed in a reaction mixture, reusing it, thereby reducing the catalyst cost and the load of succeeding steps.

The present invention will be described in more detail in the following.

A boron trifluoride complex in the present invention means a complex of boron trifluoride and various polar compounds. Boron trifluoride is apt to form a complex with polar compounds such as oxygen-containing compound, nitrogen-containing compound and sulfur-containing compound in various ratios, that is, in various molar coordination ratios. These complexes formed are used typically as catalysts for many kinds of reaction. Therefore, boron trifluoride complexes used mainly as catalyst will be described in the following.

Complexing agents used for preparing the complex catalyst in the present invention can form complexes with boron trifluoride by physical or chemical bonding strength. Exemplified as the complexing agents are organic or inorganic compounds, that is, oxygen-containing compounds such as water, alcohols, ethers, phenols, ketones, aldehydes, esters, organic acids and acid anhydrides, nitrogen-containing compounds, sulfur-containing compounds, phosphorus-containing compounds, inorganic acids and so forth. Boron trifluoride can form complexes with aromatic compounds such as benzene besides the above compounds.

Further, complexing agents which form boron trifluoride complex catalysts suitable in the present invention will be described in the following, although they do not restrict the invention.

That is, exemplified as alcohols are aromatic or $C_1$–$C_{20}$ aliphatic alcohols, where the $C_1$–$C_{20}$ hydrocarbon group may be straight-chain alkyl, branched-chain alkyl such as sec- and tert-alkyl, alicyclic, or alkyl having an alicyclic ring or rings. As examples, there are methanol, ethanol, propanol, butanol, pentanol, hexanol, heptanol, octanol, nonanol, decanol, and benzyl alcohol, cyclohexanol and so forth. Further, diols can be also used.

Exemplified as ethers are those having aromatic or $C_1$–$C_{20}$ aliphatic hydrocarbon group, where the $C_1$–$C_{20}$ hydrocarbon skeleton may be straight-chain alkyl group, branched-chanin alkyl group such as sec- and tert-alkyl, alicyclic group, or alkyl group having an alicyclic ring or rings. As examples, there are dimethyl ether, diethyl ether, methyl ethyl ether, dipropyl ether, methyl propyl ether, ethyl propyl ether, dibutyl ether, methyl butyl ether, ethyl butyl ether, propyl butyl ether, dipentyl ether, and phenyl methyl ether, phenyl ethyl ether, diphenyl ether, cyclohexyl methyl ether, cyclohexyl ethyl ether and so on.

As phenols, monohydric to trihydric phenols are suitable. More particularly, phenol and cresol are preferable.

Exemplified as ketones are those having aromatic or $C_1$–$C_6$ aliphatic hydrocarbon groups, wherein the $C_{1-6}$ hydrocarbon skeletons may be straight-chain alkyl group, branched-chain alkyl group such as sec- and tert-alkyl, alicyclic group, or alkyl group having an alicyclic ring or rings. As examples, there are methyl ethyl ketone, diethyl ketone, methyl butyl ketone, and cyclohexanone and the like.

Exemplified as esters are those obtained by esterification of aromatic or $C_1$–$C_6$ aliphatic alcohol with aromatic or $C_1$–$C_6$ aliphatic carboxylic acids, or phosphoric acid, where the $C_1$–$C_6$ hydrocarbon skeleton may be straight-chain alkyl group, branched-chain alkyl group such as sec- and tert-alkyl, alicyclic group, or alkyl group having an alicyclic ring or rings. As examples, there are methyl formate, ethyl formate, methyl acetate, ethyl acetate, propyl acetate, butyl acetate, pentyl acetate, hexyl acetate, ethyl hexanoate, ethyl benzoate, and completely esterified products of phosphoric acid such as tributyl phosphate.

Exemplified as organic acids are aromatic or $C_1$–$C_6$ aliphatic carboxylic acids or their halogen substitutes, phosphoric acid, and partially esterified products of phosphoric acid with aromatic or $C_1$–$C_6$ aliphatic alcohols, where the $C_1$–$C_6$ hydrocarbon skeleton may be straight-chain alkyl group, branched-chain alkyl group such as sec- and tert-alkyl, alicyclic group, or alkyl group having an alicyclic ring or rings. As examples, there are formic acid, acetic acid, propionic acid, oxalic acid, malonic acid, benzoic acid, diethyl phosphate and the like.

Further, exemplified as inorganic acids are phosphoric acid, hydrochloric acid and the like.

The above complexing agents in each complex system can be used alone and also as a mixture of two or more kinds thereof in appropriate ratios. A complex itself can be prepared according to the conventional methods. For example, complex may be previously prepared, and it is also possible to put boron trifluoride and one or more kinds of complexing agents in a given ratio into a reaction system separately or at once, and cause formation of a boron trifluoride complex in the reaction liquid.

The molar ratio of boron trifluoride to complexing agent is preferably in the range from 0.01:1 to 2:1. If the molar ratio of boron trifluoride to complexing agent is less than 0.01, a catalyst activity is too low to achieve the object of olefin polymerization. If the molar ratio is more than 2, boron trifluoride is too much compared with the complexing agent to keep a stable coordination, causing trouble in keeping the molar ratio of boron trifluoride in a recovered catalyst. As a result, it is necessary to adjust the molar ratio when reusing the recovered catalyst, which makes the process complicated undesirably.

In preparing a complex catalyst, it is possible to use a solvent which is appropriately inactive to the reaction and can dissolve or disperse the complex. According to the present invention, the complex can be separated and recovered easily by combining or agglomeration caused by applying an electric field. Therefore, the complex in the form of liquid is desirable. However, when a solvent is used in the above preparation, even solid complex behaves like a liquid complex and can be treated according the present invention.

In order to separate and recover a boron trifluoride complex by applying an electric field, the fluid containing the boron trifluoride complex must be electrically-nonconductive. Any fluid is not particularly restricted so long as it is electrically-nonconductive and can disperse or dissolve at least a part of boron trifluoride. As examples, there are hydrocarbon fluids, preferably aliphatic hydrocarbon fluids.

When a boron trifluoride complex is used as a catalyst, a reaction mixture containing the catalyst obtained by reaction is the object fluid to which an electric field is applied. For example, when an aromatic compound is alkylated by olefins with a boron trifluoride complex catalyst, the mixture composed of the feed, an alkyl-substituted aromatic compound as the product, and the boron trifluoride complex catalyst can be used as the object. When styrene or olefin such as isobutene is polymerized to obtain oligomer, the mixture containing the feed, oligomer and the boron trifluoride complex catalyst can be used as the object. Further, in a reaction where a $C_9$ aromatic fraction obtained from a naphtha cracker or a $C_4$ fraction containing isobutylene and others is supplied as feed to produce petroleum resin or polybutene respectively, the reaction mixture containing the feed, petroleum resin or polybutene as the product, and the boron trifluoride complex catalyst can be used as the object for applying an electric field.

The boron trifluoride complex is generally dispersed in the above electrically-nonconductive fluid. Thus, a boron trifluoride complex is hardly soluble in an electrically-nonconductive fluid. However, not only when it is just dispersed with cloudiness, but also when it is dissolved and is transparent at a glance, the complex can be separated and recovered by applying an electric field or by changing the conditions in applying an electric field. Accordingly, the form of complex in the fluid, whether dispersed or dissolved, is not so important. However, as mentioned above, the complex must be in the form of liquid, and when in the form of solid, it is liquidized for use by dissolving or dispersing in a suitable solvent.

According to the present invention which comprises applying the following direct and/or alternating voltage to an electrically-nonconductive fluid in which a boron trifluoride complex is dispersed and/or dissolved, it is possible to agglomerate and settle the dispersed and/or dissolved complex catalyst without changing the molar ratio of boron trifluoride complex to complexing agent and separate it from the reaction mixture.

In the present invention, the reason why the complex is separated by settling by applying an electric voltage is not clear, but it is surmised as follows. As for a boron trifluoride complex, it is supposed, although the complex itself or the liquid drop itself containing the complex is not charged with electricity, there is an electric polarization or an electric deviation between boron trifluoride and ligands. When an electric voltage is applied to the complex molecule, the electric polarization diminishes partially and an electric repulsion among the complex molecules disappears, so that combining or agglomeration among the complex molecules is caused. It is supposed consequently that the combined or agglomerated complex is separated by settling owing to a difference of specific gravity to form a lower layer under the electrically-nonconductive fluid containing the complex, and can be separated from the electrically-nonconductive fluid.

As an electric voltage applied to an electrically-nonconductive fluid such as hydrocarbon reaction mixture, either a direct voltage or an alternating voltage may be used. Both direct and alternating voltages can be also applied independently at once. The electric voltage can be generated by means of a conventional constant-voltage generator. An electric field strength generated from a direct and/or alternating voltage can separate the complex easily so long as it is 0.001–40 kV/mm, preferably in the range of 0.01–1 kV/mm. Further, some fluctuation of the electric voltage can be allowed. If an electric field strength is less than 0.001 kV/mm, the complex can be hardly separated by settling. On the other hand, if an electric field strength is more than 40 kV/mm, a dielectric breakdown phenomenon and side reactions such as electrolysis of the components take place. Both cases are undesirable.

A distance between the electrodes to which a direct and/or alternating voltage is applied is selected appropriately, for example, from the range of 0.1–100 cm, preferably 1–50 cm. In the present invention, any apparatus for applying an electric field can be used without any restriction on its shape or structure, so long as it contains the means of applying an electric field to the object fluid between at least one pair of electrodes. As for the shape of electrode, any shape such as plate, substantial cylinder, hollow cylinder and sphere can be used. The surface of electrode can be porous or netlike. Thus, besides parallel electrodes, these can be suitably combined into a pair of electrodes. In this case, separation efficiency can be adjusted suitably by varying the distance (space) between electrodes together with varying an electric voltage to be applied, and it is also possible to reverse the polarity of electrodes appropriately. Furthermore, plural pairs of electrodes can be combined together. Because the object fluid is electrically-nonconductive even though containing boron trifluoride complex, an electric current hardly flows when an electric voltage is applied, so that the electric power consumed is very little. In this point, the present invention is also very profitable.

The temperature of electrically-nonconductive fluid when an electric voltage is applied is not especially restricted so long as it is within the range from −100° C. to +50° C. However, when the treatment is carried out in the presence of catalyst, it is preferable to select a range of temperature lower than the reaction temperature, so as to prevent as far as possible the composition of reaction mixture from changing due to an effect of catalyst.

Further, the time interval of applying an electric voltage is not especially restricted. For example, when an electric voltage is applied in a batch type, it is usually possible to select appropriately out of the range from 1 minute to 1 hour, depending on the concentration of complex, the kind of ligand in a complex and so forth.

During the period of applying an electric voltage, the electrically-nonconductive fluid is preferably left still without stirring and the like. Although a boron trifluoride complex can be separated by only leaving still, but it can be separated and recovered much more quickly and easily by applying an electric field jointly than by only leaving still.

Although leaving still is preferable while applying an electric field, it is possible to flow an electrically-nonconductive fluid so long as the separation of complex by settling is not disturbed. Therefore, it is possible also to utilize a method which comprises flowing the fluid in an appropriate piping, applying an electric voltage to the electrodes of appropriate shape installed in the piping, and separating the complex by settling continuously.

In applying an electric voltage, if the viscosity of electrically-nonconductive fluid as the object is very high, separation of the complex catalyst by settling is insufficient. From this point of view, the viscosity of the electrically-nonconductive fluid as the object for applying an electric voltage is preferably 10,000 cP (centipoise) or less at the temperature while applying an electric voltage.

Further, it is possible to adjust the viscosity of the system within the above range for applying an electric voltage by adding an inactive solvent to the fluid.

Although the concentration of complex in the electrically-nonconductive fluid as the object for applying an electric voltage is not especially restricted, it is usually 0.001% by weight or more preferably. If the concentration of complex is too low, there is a tendency that the effect by applying an electric voltage is not demonstrated sufficiently. Though the upper limit is not set, it is usually 10% by weight or less.

In a reaction which is carried out with boron trifluoride as catalyst, the catalyst is prepared by coordinating complexing agents selected depending on the object reaction in appropriate ratios.

Exemplified as reactions using boron trifluoride as catalyst are those which comprises contacting an aromatic compound and an olefin with a boron trifluoride complex catalyst to promote alkylation, and obtaining alkyl-substituted aromatic compounds. As examples, there is alkylation in which aromatic compounds such as benzene, toluene and xylene, and olefins such as ethylene, propylene, butene and butadiene are used.

Exemplified as reaction solvents in the above reactions are hydrocarbons inactive to the reaction, that is, n-paraffin such as n-butane and isoparaffin such as isobutane and isooctane, and also the reaction feed itself such as benzene and toluene. With the alkylations, for example, ethylbenzene, propylbenzene, butylbenzene and butenylbenzene are produced.

Further, exemplified as reactions using boron trifluoride as catalyst are also those which comprises polymerizing one or more kinds of unsaturated aromatic compounds such as styrene and vinyl toluene or olefins such as butene and isobutene. Exemplified as solvents for the reactions are hydrocarbons inactive to the reaction, that is, n-paraffin such as n-butane and isoparaffin such as isobutane and isooctane, and also the reaction feed itself. With the polymerizations, olefin oligomers of relatively low molecular weight are produced. For example, oligomer of styrene or isobutene can be obtained.

By using as a reaction feed the fractions from a naphtha cracker, for example, a $C_9$ aromatic fraction containing aromatic olefins such as vinyl toluene, a $C_5$ fraction containing aliphatic olefins such as piperylene, or a $C_4$ fraction containing olefins such as 1-butene and trans- or cis-2-butene besides isobutylene, aromatic or aliphatic petroleum resin or polybutene can be obtained.

In polymerizing olefins, boron trifluoride complex catalysts are often used. If the above method for recovering a boron trifluoride complex can be utilized for this polymerization, cost of catalyst can be reduced, and further environmental pollution due to the catalyst residue can be avoided, so that a considerable amount of profit is obtained.

Then, a process for polymerizing olefin with a boron trifluoride complex catalyst, for recovering the complex catalyst after polymerization, and for reusing the recovered catalyst will be described as follows, which overlaps the above descriptions partially.

More particularly, the above process for recovering and reusing is comprised of the following steps from (I) to (IV):

(I) polymerizing olefin in a liquid phase in the presence of a boron trifluoride complex catalyst comprised of boron trifluoride and complexing agent, (II) after polymerization, applying a direct and/or alternating voltage to a reaction mixture in which a boron trifluoride complex catalyst is at least partly dispersed and/or dissolved to thereby separate the complex catalyst by settling owing to a difference of specific gravity, (III) recovering the complex catalyst separated by settling from the reaction mixture, and (IV) polymerizing olefin in a liquid phase using at least a part of the recovered complex catalyst.

First, in the step (I), olefin is polymerized in a liquid phase in the presence of a boron trifluoride complex catalyst comprised of boron trifluoride and a complexing agent.

Olefins to be used here are mainly butadiene, isobutene, butene-1 and cis- or trans-butene-2. Besides these, however, any olefin can be used so long as its cationic polymerization can be caused by a boron trifluoride complex catalyst. For example, other than the above $C_4$ olefins, $C_2$–$C_{20}$ aliphatic olefins such as ethylene, propylene, isoprene, pentene and hexene-1, $C_8$–$C_{10}$ aromatic olefins such as styrene and vinyl toluene, and alicyclic olefins such as DCPD can be used as feed. These olefins may be used for polymerization either alone or as a mixture thereof.

In polymerization, the concentration of olefin is preferably within the range of 5–100% by weight. If the concentration of olefin is less than 5% by weight, an economical loss in practice is undesirably great. Besides olefins, solvents which are inactive to reaction can be appropriately used, for example, hydrocarbons including n-paraffins such as n-butane and isoparaffins such as isobutane and isooctane. Exemplified as industrial feeds are $C_5$ fraction containing aliphatic olefins such as piperylene, and $C_4$ fraction containing olefins such as 1-butene and trans- or cis-2-butene, and further isobutene and n-butane.

As mentioned before, inorganic or organic polar compounds can be used as complexing agents which form a complex with boron trifluoride. Exemplified as the polar compounds are, as the above, water, alcohols, ethers, phenols, ketones, aldehydes, esters, organic or inorganic acids, and acid anhydrides.

The molar ratio of boron trifluoride to complexing agent in a complex can be in the range of 0.01:1–2:1, as mentioned above.

In the above reaction, boron trifluoride in a catalyst is usually used in the ratio of 0.0001–0.5 mol to 1 mol of olefin to be polymerized. The reaction itself can be carried out according to the conventional methods, either in a batch type or in a flow type. Although the reaction temperature and the reaction time are not especially restricted, it is preferable to select the temperature from the range from −100° C. to +100° C. and the time from the range from 1 minute to 4 hours.

Then, in the step (II), a direct and/or alternating voltage is applied to the reaction mixture in which boron trifluoride is at least partly dispersed and/or dissolved to thereby separate the complex catalyst by settling owing to a difference of specific gravity.

In liquid phase polymerization of olefin, the reaction mixture is obtained, which is comprised of the produced olefin oligomer, unused reactants and a boron trifluoride complex catalyst dispersed or dissolved therein.

The number average molecular weight of the olefin oligomer which is obtained by polymerizing olefin in a liquid phase is preferably in the range of 100–100,000. If the molecular weight is less than 100, it is too small for useful olefin oligomer. If the molecular weight is more than 100,000, the amount of a diluting solvent necessary for separation increases too much to be economical.

In applying an electric voltage, if the viscosity of the object reaction mixture is extremely high, a complex catalyst can not be separated by settling sufficiently. From this point of view, the viscosity of the reaction mixture as the object for applying an electric voltage is preferably 10,000 cP (centipoise) or less at the temperature when applying an electric voltage. In order to adjust the temperature within this range, an inactive solvent can be appropriately added to the reaction mixture to which an electric voltage is applied.

By applying an electric voltage to the reaction mixture containing a complex catalyst by means of the above method, the complex catalyst is separated by settling to form a lower layer in the reaction mixture. In other words, the complex catalyst which is dispersed or dissolved is agglomerated or combined together by applying an electric voltage and separated by settling owing to a difference of specific gravity.

The conditions in applying an electric voltage such as electric field strength and a distance between electrodes are as mentioned before. That is, electric field strength can be in the range of 0.001–40 kV/mm, and the temperature in the range from −100° C. to +50° C. The time for separation by settling is not especially restricted as mentioned before, and usually can be selected from the range from 1 minute to 1 hour depending on the extent of leaving still.

Then, in the step (III), the complex catalyst separated by settling from the reaction mixture is recovered.

By withdrawing the complex catalyst separated by settling continuously or intermittently with appropriate means from the reaction system, the complex catalyst can be recovered from the reaction mixture.

Furthermore, in the step (IV), olefin is polymerized in a liquid phase using at least a part of the recovered complex catalyst.

Because the molar coordination ratio of the complex catalyst which has settled to form a lower layer is substantially not changed from that before use in the reaction, the catalyst has the same activity as before and can be reused as it stands for the reaction. Thus, by reusing catalyst, it is possible to reduce the catalyst cost.

In the second or later reaction, a new boron trifluoride complex catalyst can be added appropriately. For example, the complex catalyst is supplemented with the new one by the amount corresponding to that of the complex catalyst which has been lost out of the reaction system together with olefin oligomer. Further, it is possible not only to supplement the complex itself, but also to add boron trifluoride and a complexing agent as complex components simultaneously or separately. Furthermore, when reusing the recovered catalyst, diluting agents can be added appropriately.

In polymerizing olefin where the catalyst is reused, the same reaction conditions can be used as in the initial polymerization. For example, it is possible to polymerize olefin continuously, separate and recover the catalyst at the same time by the present method of applying an electric voltage, and recycle the recovered catalyst into the polymerization zone continuously or intermittently. However, as for the recovered catalyst, appropriately varied polymerization conditions can be also used.

After separating catalyst from the reaction mixture, the objective olefin oligomer can be obtained by an appropriate separating means such as distillation. When a little of complex catalyst remains in the olefin oligomer obtained, it can be removed if necessary by the conventional methods of removing catalyst, for example, an appropriate neutralization step. The removal of the remained complex catalyst can be carried out easily, because almost all complex catalyst has been already removed.

BRIEF DESCRIPTION OF DRAWING

The FIGURE is a graph showing the results of measurement on $^{13}$C-NMR spectra of a boron trifluoride diethyl ether complex before and after reaction.

BEST METHOD FOR CARRYING OUT THE INVENTION

In the following, the present invention will be described in more detail with examples.

<Production of Boron Trifluoride Complex Catalyst>

A complex catalyst was prepared by injecting boron trifluoride (purity 99.7%) into a complexing agent kept below 0° C. while restraining the increase of temperature, until molar coordination ratio reached the predetermined value. Not particularly mentioned in detail, the complexes susceptible to decomposition were prepared and preserved below the decomposition temperature and served.

<Equipments for Experiment>

A 1-liter four neck flask is equipped with a pipe for introducing nitrogen gas, a stirring apparatus, a bomb for storing gas, a pipe for injecting gas, a thermometer and a cooling vessel at low temperature, and parallel electrodes comprised of two flat plates are installed in the flask with a distance of 5 mm. Further, an external electric source which can provide a stable direct or alternating voltage is secured, and the two output lines are connected with each of two parallel electrodes. However, the external electric source is kept suspended until an electric voltage is applied after the end of reaction.

EXAMPLE 1

Under a nitrogen flow, the above flask was charged with 100 g of isooctane (extra pure) as diluting solvent, and provided with pure isobutene while being kept −25° C. with stirring in the flask, and then supplied with 2.09 g of boron trifluoride diethyl ether complex (1:1 mol adduct), thereafter reaction was carried out for 30 minutes with stirring violently.

After the reaction, a 500 V direct voltage was applied to two parallel electrodes in the reaction solution kept −25° C. from an external electric source for 30 minutes, whereupon 198.3 g of colorless, transparent upper layer liquid and 1.78 g of colorless, transparent lower layer liquid were separated with an interface formed.

The upper layer only was withdrawn, neutralized with a dilute aqueous solution of sodium hydroxide, and then distilled by a vacuum distillation to remove isooctane and lighter fraction, after that the conversion of isobutene participating in the polymerizing reaction and the yield of olefin oligomer produced were determined.

The lower layer was preserved in another vessel. The above flask was charged again with 100 g of isooctane as diluting solvent, and provided anew with 100 g of isobutene while being kept −25° C. with stirring in the flask, and then supplied with 0.31 g of boron trifluoride diethyl ether complex corresponding to the amount of that lost in the first reaction and 1.78 g of the complex preserved in the other vessel together, after that polymerizing reaction was carried out.

After the reaction, a 500 V direct voltage was applied into the reaction solution from an external electric source for 30 minutes similarly as in the first time to carry out the separation with an interface formed. The upper layer only was withdrawn similarly as in the first time, and neutralized with a dilute aqueous solution of sodium hydroxide, after that the conversion and the yield were determined.

The above procedure was repeated three times, that is, four polymerizing reactions were carried out successively.

The lower layer liquid obtained after the first polymerizing reaction was measured by $^{13}$C-NMR.

The FIGURE is a measurement on $^{13}$C-NMR spectra of a boron trifluoride diethyl ether complex before and after the use in a reaction. The numerals on the axis of abscissa indicate the chemical shifts expressed in ppm as compared with the peak of tetramethylsilane (TMS). In the measurement by $^{13}$C-NMR, boron trifluoride diethyl ether complex having the molar coordination ratio of 1.0:1.0 shows two peaks of 12.9 ppm and 69.9 ppm due to carbon atoms of diethyl ether. When the molar ratio is varied, two peaks show shifting. However, when a $^{13}$C-NMR measurement was carried out on a sample of the boron trifluoride diethyl ether complex obtained after the end of reaction, peaks were found at the same locations as those measured in an unused complex catalyst. Thus, it was found out that the complex had the same molar ratio as before the reaction.

The results on polymerization in the upper layer and the ratio of the amount of the complex catalyst settled down in the lower layer to its amount charged (recovery) in the first and fourth reactions will be shown in Table 1.

TABLE 1

| Reaction Order | Conversion of Isobutene | Yield of Oligomer | Recovery of Complex Catalyst |
|---|---|---|---|
| 1 | 98.0 mol % | 94.7 wt % | 85.1% |
| 4 | 97.7 mol % | 93.8 wt % | 84.7% |

EXAMPLE 2

After polymerizing reaction was carried out in the same way as in Example 1, a 500 V alternating voltage was applied into the reaction mixture for 30 minutes, whereupon 197.5 g of colorless, transparent upper layer liquid and 1.71 g of colorless, transparent lower layer liquid were separated with an interface formed.

Similarly as in Example 1, the upper layer only was treated subsequently, and the conversion of isobutene and the yield of olefin oligomer were determined.

The lower layer was preserved in another vessel. The above flask was charged again with isooctane and isobutene, and then supplied with 0.38 g of boron trifluoride diethyl ether complex (1:1 mol adduct) lost in the first reaction and 1.71 g of the complex preserved in the other vessel together, after that polymerizing reaction was carried out.

The above procedure was repeated three times, that is, four polymerizing reactions were carried out successively. The results on polymerization in the upper layer and the ratio of the amount of the complex catalyst settled down in the lower layer to its amount charged (recovery) in the first and fourth reactions will be shown in Table 2.

TABLE 2

| Reaction Order | Conversion of Isobutene | Yield of Oligomer | Recovery of Complex Catalyst |
|---|---|---|---|
| 1 | 97.9 mol % | 94.5 wt % | 81.8% |
| 4 | 97.8 mol % | 93.6 wt % | 80.7% |

EXAMPLE 3

Polymerizing reaction was carried out in the same way as in Example 1, except for using 1.69 g of boron trifluoride ethanol complex (1:1 mol adduct) as a complex catalyst.

After the reaction, a 500 V direct voltage was applied to two parallel electrodes in the reaction solution kept −25° C. from an external electric source for 30 minutes, whereupon 198.3 g of colorless, transparent upper layer liquid and 1.44 g of colorless, transparent lower layer liquid were separated with an interface formed.

Similarly as in Example 1, the upper layer only was treated subsequently, and the conversion of isobutene and the yield of olefin oligomer were determined.

The lower layer liquid obtained after the first polymerizing reaction was measured by $^{13}$C-NMR similarly as in Example 1, whereupon it was found out that the catalyst was boron trifluoride ethanol and did not varied in molar coordination ratio.

The lower layer was preserved in another vessel. The above flask was charged again with 100 g of isooctane as diluting solvent, and provided anew with 100 g of isobutene while being kept −25° C. with stirring in the flask, and then supplied with 0.25 g of boron trifluoride ethanol complex (1:1 mol adduct) corresponding to the amount of that lost in the first reaction and 1.44 g of the complex preserved in the other vessel together, after that polymerizing reaction was carried out.

The above procedure was repeated three times, that is, four polymerizing reactions were carried out successively. The results on polymerization in the upper layer and the ratio of the amount of the complex catalyst settled down in the lower layer to its amount charged (recovery) in the first and fourth reactions will be shown in Table 3.

TABLE 3

| Reaction Order | Conversion of Isobutene | Yield of Oligomer | Recovery of Complex Catalyst |
|---|---|---|---|
| 1 | 98.3 mol % | 78.5 wt % | 85.2% |
| 4 | 97.5 mol % | 77.3 wt % | 83.8% |

EXAMPLE 4

Polymerization of isobutene was carried out using isobutane as solvent. That is, a flask was charged with 200.0 g of isobutene diluted with isobutane, and then supplied with 1.64 g of boron trifluoride diethyl ether complex (1:1 mol adduct) while being kept 125° C., thereafter reaction was carried out for 30 minutes with stirring violently.

After leaving still, a 500 V direct voltage was applied to two parallel electrodes in the reaction solution kept −25° C. from an external electric source for 30 minutes, whereupon 193.5 g of colorless, transparent upper layer liquid and 1.39 g of colorless, transparent lower layer liquid were separated with an interface formed.

Similarly as in Example 1, the upper layer only was treated subsequently, and the conversion of isobutene and the yield of olefin oligomer were determined.

The lower layer was preserved in another vessel. The above flask was charged again with isobutane and isobutene, and then supplied with 0.25 g of boron trifluoride diethyl ether complex corresponding to the amount of that lost in the first reaction and 1.39 g of the complex preserved in the other vessel together, thereafter polymerizing reaction was carried out.

The above procedure was repeated three times, that is, four polymerizing reactions were carried out successively. The results on polymerization in the upper layer and the ratio of the amount of complex catalyst settled down in the lower layer to its amount charged (recovery) in the first and fourth reactions will be shown in Table 4.

TABLE 4

| Reaction Order | Conversion of Isobutene | Yield of Oligomer | Recovery of Complex Catalyst |
|---|---|---|---|
| 1 | 89.5 mol % | 85.3 wt % | 84.8% |
| 4 | 88.5 mol % | 84.7 wt % | 84.2% |

COMPARATIVE EXAMPLES 1–4

In Comparative Examples 1–4, polymerizations were carried out in the same conditions as in the first polymerizing reactions of Examples 1–4 respectively, but any electric voltage was not applied to the reaction mixtures.

While they were left still after the reaction with its temperature being kept, the boron trifluoride complex catalyst in every Example was held in the state of being dispersed in the reaction liquid, and was not separated by settling as it was.

INDUSTRIAL APPLICABILITY

The present method, wherein the electric current flowing through a fluid by applying an electric voltage is zero or very weak, hardly consume the electric power and is economical. Moreover, it does not change the composition of the fluid such as reaction mixture and does not give any other effect than separating boron trifluoride complex. Therefore, it can present an industrially useful process.

Furthermore, in producing olefin oligomer using a boron trifluoride complex catalyst for the reaction, it is possible to separate the complex catalyst by settling from the reaction system and recover it in an industrially economical and easy way by applying a direct and/or alternating voltage into the reaction mixture produced. Moreover, the catalyst does not lose its activity and can be utilized repeatedly.

The conventional processes for separating and removing the used catalyst utilize the methods which comprise neutralizing with aqueous solutions of basic substances such as ammonia and caustic soda and washing out by water. From the washing process, a large quantity of waste water containing fluorides as neutralized products of used alkaline compound and boron trifluoride has been discharged. By recovering the catalyst in a high recovery according to the preset invention, the problems of environmental pollution accompanied with the disposal of industrial wastes can be greatly reduced.

What is claimed is:

1. A method of recovering a boron trifluoride complex formed by contacting boron trifluoride with a complexing agent comprising the steps of applying direct and/or alternating voltage to an electrically-nonconductive fluid in which at least a part of boron trifluoride complex is dispersed and/or dissolved so as to separate said boron trifluoride complex by settling from said electrically-nonconductive fluid, and recovering then the separated complex.

2. A method of recovering a boron trifluoride complex as claimed in claim 1, wherein the electric field strength of said direct and/or alternating voltage is in the range of 0.001–40 kV/mm.

3. A method of recovering a boron trifluoride complex as claimed in claim 1, wherein the temperature of the electrically-nonconductive fluid while applying said direct and/or alternating voltage is in the range of −100° C. to +50° C.

4. A method of recovering a boron trifluoride complex as claimed in claim 1, wherein said complexing agent is a polar compound.

5. A method of recovering a boron trifluoride complex as claimed in claim 4, wherein said polar compound is one member selected from the group consisting of water, alcohols, ethers, phenols, ketones, aldehydes, esters, acid anhydrides and acids.

6. A method of recovering a boron trifluoride complex as claimed in claim 1, wherein the molar ratio of boron trifluoride to complexing agent in said complex is in the range of 0.01:1 to 2:1.

7. A method of recovering a boron trifluoride complex as claimed in claim 1, wherein said electrically-nonconductive fluid is a hydrocarbon fluid.

8. A process for producing olefin oligomer which comprises the following steps of (I) to (IV):

(I) polymerizing olefin in a liquid phase in the presence of a boron trifluoride complex catalyst which comprises boron trifluoride and a complexing agent, (II) after polymerization, applying a direct and/or alternating voltage to a reaction mixture in which at least a part of the boron trifluoride complex catalyst is dispersed and/or dissolved, so as to separate the complex catalyst by settling owing to the difference of specific gravities, (III) recovering the complex catalyst separated by settling from the reaction mixture, and (IV) polymerizing olefin in the liquid phase using at least a part of the recovered complex catalyst.

9. A process for producing olefin oligomer as claimed in claim 8, wherein the concentration of olefin in a feed mixture in said liquid phase polymerization is 5% by weight or more.

10. A process for producing olefin oligomer as claimed in claim 8, wherein the molecular weight of said olefin oligomer is in the range of 100–100,000.

* * * * *